(12) United States Patent
Kroepke et al.

(10) Patent No.: US 9,314,651 B2
(45) Date of Patent: Apr. 19, 2016

(54) ACTIVE INGREDIENT COMBINATIONS OF GLUCOSYL GLYCERIDES AND ONE OR MORE ACIDIC PRESERVATIVES

(75) Inventors: Rainer Kroepke, Schenefeld (DE); Christian Frese, Hamburg (DE); Cathrin Scherner, Norderstedt (DE); Svenja Lena Moellgaard, Hamburg (DE); Sven Fey, Hamburg (DE)

(73) Assignee: BEIERSDORF AG, Hamburg (DE)

( * ) Notice: Subject to any disclaimer, the term of this patent is extended or adjusted under 35 U.S.C. 154(b) by 122 days.

(21) Appl. No.: 13/996,615

(22) PCT Filed: Nov. 28, 2011

(86) PCT No.: PCT/EP2011/071175
§ 371 (c)(1),
(2), (4) Date: Sep. 18, 2013

(87) PCT Pub. No.: WO2012/084418
PCT Pub. Date: Jun. 28, 2012

(65) Prior Publication Data
US 2014/0005130 A1 Jan. 2, 2014

(30) Foreign Application Priority Data
Dec. 23, 2010 (DE) .......................... 10 2010 055 838

(51) Int. Cl.
| A61K 8/368 | (2006.01) |
| A61K 8/365 | (2006.01) |
| A61K 8/60 | (2006.01) |
| A61K 8/36 | (2006.01) |
| A61Q 5/00 | (2006.01) |
| A61Q 5/02 | (2006.01) |
| A61Q 5/12 | (2006.01) |
| A61Q 19/10 | (2006.01) |

(52) U.S. Cl.
CPC ... *A61Q 5/00* (2013.01); *A61K 8/36* (2013.01); *A61K 8/365* (2013.01); *A61K 8/368* (2013.01); *A61K 8/602* (2013.01); *A61Q 5/02* (2013.01); *A61Q 5/12* (2013.01); *A61Q 19/10* (2013.01)

(58) Field of Classification Search
None
See application file for complete search history.

(56) References Cited

U.S. PATENT DOCUMENTS

| 5,916,967 A * | 6/1999 | Jones et al. ................... 524/732 |
| 5,945,093 A * | 8/1999 | Duvel ...................... A61K 8/42 |
| | | 424/70.11 |
| 2006/0165636 A1 | 7/2006 | Hasebe et al. |
| 2009/0130223 A1 | 5/2009 | Breitenbach et al. |

FOREIGN PATENT DOCUMENTS

| DE | 102005023639 A1 | 11/2006 |
| DE | 102006055043 A1 | 5/2008 |
| EP | 1602354 A1 | 12/2005 |
| EP | 1923045 A1 | 5/2008 |
| JP | 2007137862 A | 6/2007 |
| JP | 2008/024628 * | 2/2008 |
| JP | 2008024628 A | 2/2008 |

OTHER PUBLICATIONS

Database GNPD [Online] MINTEL; "Moisturizing Eye Contour", Oct. 2010.
Database GNPD [Online] MINTEL; "Moisturizing Eye Cream", Sep. 2010.

* cited by examiner

*Primary Examiner* — Traviss C McIntosh, III
(74) *Attorney, Agent, or Firm* — Abel Law Group, LLP

(57) ABSTRACT

Active ingredient combinations of (i) acidic preservatives and (ii) one or more glucosyl glycerides.

20 Claims, No Drawings

000000000# ACTIVE INGREDIENT COMBINATIONS OF GLUCOSYL GLYCERIDES AND ONE OR MORE ACIDIC PRESERVATIVES

BACKGROUND OF THE INVENTION

1. Field of the Invention

The present invention relates to active ingredient combinations of glyceryl glucosides and one or more acidic preservatives and the use thereof in the field of cosmetic and pharmaceutical dermatology.

In particular, the present invention relates to active ingredients and cosmetic or dermatological preparations containing such active ingredient combinations.

The present invention preferably relates to detergent cosmetic preparations.

2. Discussion of Background Information

The outermost layer of the epidermis, the stratum corneum (horny layer), is an important barrier layer of particular importance for, inter alia, protection against environmental influences and from drying out. The horny layer is continuously worn away in contact with the environment and must therefore be continuously renewed.

A skin model widely used in professional circles today regards the stratum corneum as a two-component system similar to a brick wall (brick and mortar model). In this model, the corneocytes (horny cells) correspond to the bricks, while the complex composite lipid membrane in the intercellular spaces corresponds to the mortar.

Apart from their barrier effect against external chemical and physical influences, the epidermal lipids also contribute to the cohesion of the horny layer and affect the skin smoothness. In contrast to the sebaceous gland lipids which do not form a closed film on the skin, the epidermal lipids are distributed over the whole horny layer.

The extremely complex interaction of the moisture-binding substances and the lipids of the outer skin layers is very important for the regulation of skin moisture. Therefore, cosmetics generally comprise water-binding substances in addition to balanced lipid mixtures and water. These include, inter alia, polyols such as glycerol, sorbitol and xylitol, ethoxylated polyols and hydrolysed proteins. Substances contained in the so-called natural moisturising factor (NMF) are further used, such as urea, carbohydrates (e.g. glucose) and amino acids (e.g. serine). These substances are therefore particularly important for the care performance of a cosmetic product, especially due to their relatively good skin and mucous membrane compatibility.

The desire for clean skin is probably as old as humankind, since dirt, sweat and residual dead skin particles offer the ideal breeding ground for pathogens and parasites of every type. The desire for personal hygiene steadily increased since in the 60s of the $20^{th}$ century, in addition to "classical" soap, liquid detergents with newly developed synthetic surfactants were also formulated. Since then, bathing and showering are now indispensable in our daily life. Nowadays, a variety of products for the cleaning of various parts of the body are available to consumers.

Cleaning means the removal of (environmental) dirt and this causes an increase in physical and mental well-being. The cleaning of the surface of skin and hair is a very complex process dependent on many parameters. Firstly, external substances, such as hydrocarbons or inorganic pigments from different environments and also residues of cosmetics or even undesired microorganisms should be removed as completely as possible. Secondly, endogenous secretions such as sweat, sebum, skin flakes and hair dandruff should be washed off without profound changes to the physiological equilibrium.

The preserving of cosmetic preparations is a difficult task, since, on the one hand, a sufficient preservation to protect the formulation from bacterial contamination must be ensured while, on the other hand, negative influences of the preservative on the compatibility, stability and organoleptic properties of the formulation must be avoided. The preservatives must therefore be effective, toxicologically harmless, well tolerated by skin, be stable to formulation and inexpensive to produce.

A large number of preservatives, such as formaldehyde eliminators, parabens, phenols and derivatives thereof, bisguanidines and halogenated compounds, have a high antimicrobial efficacy, but can however cause skin irritation and allergic reactions and are therefore regarded critically by consumers and mostly regarded as undesirable.

One class of preservatives which are characterized by good compatibility are the organic acids effective as preservatives, particularly salicylic acid, benzoic acid, propionic acid, dehydroacetic acid (3-acetyl-6-methyl-2H-pyran-2,4(3H)-dione) and sorbic acid or the physiologically compatible water-soluble metal salts thereof.

A disadvantage of these preservatives is the fact that they are effective only at relatively high concentrations and at acidic pH. Thus, incorporation of the acids in the preparations is difficult and limited. In addition, the required concentrations lead to an impairment of the organoleptic properties and have an adverse effect on the stability of the formulation.

Thus, there is a need for preparations which overcome the disadvantages of the prior art.

SUMMARY OF THE INVENTION

Following this, it was surprising and unpredictable that active ingredient combinations of
 (i) one or more acidic organic acids which are effective as preservatives and
 (ii) one or more glucosyl glycerides
or cosmetic preparations containing such active ingredients combinations eliminate the disadvantages of the prior art.

DETAILED DESCRIPTION OF THE INVENTION

Surprisingly, it was established that combinations of organic acids effective as preservatives with glucosyl glycerides can overcome the disadvantages of the prior art.

These preparations are characterized by a good antimicrobial efficacy, good skin tolerability and excellent organoleptic properties compared to preparations of the prior art. In addition, these preparations have an improved stability.

Preferred organic acids effective as preservatives are salicylic acid, benzoic acid, propionic acid, dehydroacetic acid (3-acetyl-6-methyl-2H-pyran-2,4(3H)-dione) and sorbic acid. Salicylic acid, benzoic acid and dehydroacetic acid are particularly preferred. Salicylic acid and benzoic acid are especially preferred. The use of physiologically compatible water-soluble metal salts of these acids is also preferred.

The concentration of the preservatives is preferably 0.0001 to 10%, particularly preferably 0.005-5%, particularly preferably 0.01%-3%.

In addition, the rinse-off preparations contain surfactants, thickeners, preservatives, perfume, oils and optionally further cosmetic ingredients.

Advantageously in the sense of the present invention, glucosyl glycerides of the general formula

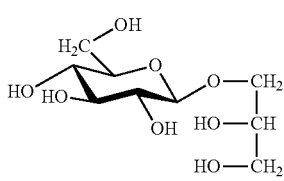

and/or of the general formula

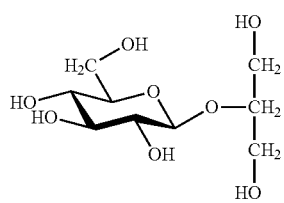

and/or of the general formula

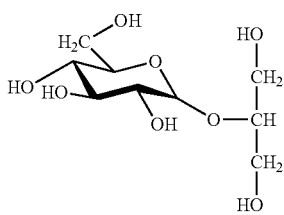

and/or of the general formula

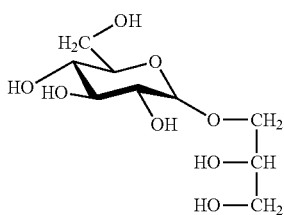

are preferred in accordance with the invention.

Particularly advantageous according to the invention are those preparations which are characterized in that the glucosyl glyceride(s) are present in the water and/or oil phase at concentrations of 0.001-40.00% by weight, preferably 0.005-15.00% by weight, particularly preferably 0.01-12.00% by weight, based in each case on the total weight of the composition.

Advantageously, in accordance with the invention, the molar ratio of one or more glucosyl glycerides to one or more organic acids which are effective as acidic preservatives is selected from the range of 100:1 to 1:100, preferably 50:1 to 1:50, particularly preferably 20:1 to 1:20.

The use of the preparation according to the invention as a cosmetic cleaning preparation is advantageous in accordance with the invention. The preparation according to the invention is preferably used as a shower gel, foam bath and bath soak, shampoo and/or facial cleanser.

It is advantageous according to the invention if the inventive cosmetic preparation is stored in a bottle, squeeze bottle, pump spray or aerosol can and is dispensed therefrom. Accordingly, bottles, squeeze bottles, double-chamber packing means, pump spray cans or aerosol cans which contain a preparation according to the invention are in accordance with the invention.

The preparation according to the invention advantageously comprises one or more anionic surfactants. According to the invention, these are advantageously present in the preparation in a concentration of 1 to 20% by weight, and according to the invention preferably in a concentration of 5 to 12% by weight, in each case based on the total weight of the preparation. According to the invention particular preference is given here to the use of sodium lauryl ether sulfate as anionic surfactant.

The preparation according to the invention advantageously comprises one or more amphoteric surfactants. According to the invention, these are advantageously present in the preparation at a concentration of 1 to 20% by weight, and according to the invention preferably in a concentration of 3 to 8% by weight, in each case based on the total weight of the preparation. According to the invention particular preference is given here to the use of cocamidopropyl betaine as amphoteric surfactant.

Moreover, the preparation according to the invention may advantageously also contain non-ionic surfactants. Particular preference is given here, according to the invention, to the use of PEG-7 glyceryl cocoate and/or PEG-40 hydrogenated castor oil as non-ionic surfactant.

It is likewise advantageous, within the context of the present invention, to add cationic polymers to the preparations. Suitable cationic polymers are, for example,
  quaternized cellulose derivatives, such as polyquaternuim-10, as are commercially available under the names Celquat and Polymer JR
  cationic guar derivatives, such as in particular the products sold under the trade names Cosmedia Guar and Jaguar
  polymeric dimethyldiallylammonium salts and copolymers thereof with esters and amides of acrylic acid and methacrylic acid, such as in particular the products commercially available under the names Merquat 100 and Merquat 550.

Within the context of the present invention, it is especially advantageous to use cationic polymer or mixtures of cationic polymers in a concentration of 0.01 to 2% by weight, preferably in a concentration of 0.05 to 1.5% by weight and particularly preferably from 0.1 to 1.0% by weight, in each case based on the total weight of the preparation.

Apart from the aforementioned substances, the compositions according to the invention optionally comprise the additives customary in cosmetics, for example, perfume, dyes, antimicrobial substances, refatting agents, complexing and sequestering agents, pearlescent agents, plant extracts, vitamins, active ingredients, preservatives, bactericides, pigments which have a coloring effect, thickeners, softening, moisturizing and/or humectant substances, or other customary constituents of a cosmetic or dermatological formulation such as alcohols, polyols, polymers, foam stabilizers, electrolytes, organic solvents or silicone derivatives.

The active ingredients, auxiliaries and additives which can be used advantageously according to the invention are here in no way limited to the substances and compounds mentioned here by name.

Active ingredients which are particularly advantageous according to the invention are in particular niacinamide, panthenol, polidocanol, [gamma]-oryzanol, ubiquinones (in particular Q-10), creatin, creatinine, biotin (vitamin H), vitamin E and vitamin E acetate, plant extracts, such as bamboo extract, water lily extract, the alpha-hydroxyacids, such as citric acid, tartaric acid, malic acid, salts such as calcium salts or sea minerals, BHT, propyl gallate and UV filters (e.g. particularly advantageously benzophenone-4).

According to the invention, active ingredients of this type can advantageously be present in the preparations in concentrations (individual concentration of an active ingredient) of 0.001 to 5% by weight, in each case based on the total weight of the preparation.

According to the invention, it is also advantageous if effect substances (e.g. colored beads and/or active ingredient beads, glitter substances etc.) are added to the preparations according to the invention and/or the preparation is provided with stable air bubbles and blisters.

Opacifiers/pearlescent agents or mixtures advantageous according to the invention are inter alia:

PEG-3 distearate (e.g. CUTINA TS from Cognis),
a combination of glycol distearate, glycerol, laureth-4 and cocamidopropyl betaine (e.g. Euperlan PK 3000 and Euperlan PK 4000 from Cognis),
a combination of glycol distearate, cocoglucosides, glyceryl oleate and glyceryl stearate (e.g. Lamesoft™ Benz from Cognis),
styrene/acrylate copolymers (e.g. Acusol OP 301 from Rohm & Haas).

It is likewise advantageous to add customary antioxidants to the preparations within the context of the present invention. According to the invention, favorable antioxidants which may be used are all antioxidants that are suitable or customary for cosmetic and/or dermatological applications.

The amount of antioxidants (one or more compounds) in the preparations is preferably 0.001 to 30% by weight, particularly preferably 0.05-20% by weight, in particular 1-10% by weight, based on the total weight of the preparation.

If the cosmetic or dermatological preparation within the context of the present invention is a solution or emulsion or dispersion, solvents which can be used are:

water or aqueous solutions
oils, such as triglycerides of capric acid or of caprylic acid, but preferably castor oil;
fats, waxes and other natural and synthetic fatty bodies, preferably esters of fatty acids with alcohols of low carbon number, e.g. with isopropanol, propylene glycol or glycerol, or esters of fatty alcohols with alkanoic acids of low carbon number or with fatty acids;
alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

In particular, mixtures of the aforementioned solvents are used. In the case of alcoholic solvents, water may be a further constituent.

Cosmetic preparations within the context of the present invention can also be present as gels which comprise, besides an effective content of the active ingredient according to the invention and solvents customarily used therefor, preferably water, also organic thickeners, e.g. gum arabic, xanthan gum, sodium alginate, cellulose derivatives, preferably methylcellulose, hydroxymethylcellulose, hydroxyethylcellulose, hydroxypropylcellulose, hydroxypropylmethylcellulose or inorganic thickeners, e.g. aluminum silicates such as bentonites, or a mixture of polyethylene glycol and polyethylene glycol stearate or distearate.

Embodiments of the present invention that are advantageous according to the invention are characterized in that the preparation likewise comprises polyacrylates as thickeners.

Polyacrylates advantageous according to the invention are polymers of acrylic acid, in particular those which are selected from the group of the so-called carbomers or carbopols (Carbopol® is actually a registered trademark of B. F. Goodrich Company). Advantageous carbopols are, for example, the grades 907, 910, 934, 940, 941, 951, 954, 980, 981, 1342, 1382, 2984 and 5984 or else the grades ETD (easy-to-disperse) 2001, 2020, 2050, Aqua-SFI, where these compounds can be present individually or in any desired combinations with one another.

Also advantageous within the context of the present invention are the copolymers of C10-C30-alkyl acrylates and one or more monomers of acrylic acid, of methacrylic acid or esters thereof that are comparable with the acrylate-alkyl acrylate copolymers.

The INCI name for such compounds is "Acrylates/C 10-30 Alkyl Acrylate Crosspolymer". Those available under the trade names Pemulen TR1 and Pemulen TR2 from B.F. Goodrich Company are particularly advantageous.

According to the invention, it is particularly advantageous if C10 to C30-alkyl acrylate copolymers are used as polyacrylates.

The thickener is present in the gel e.g. in an amount between 0.1 and 30% by weight, preferably between 0.5 and 15% by weight.

Advantageous embodiments of the present invention follow.

| Trade name | INCI | Active content | Manufacturer |
|---|---|---|---|
| Cetiol HE | PEG-7 glyceryl cocoate | 100% | Cognis |
| DC 5-7139 | Dimethicone + cocamidopropyl betaine + C12-15 pareth-3 + guar hydroxypropyltrimonium chloride | 65% + 1% + 1% + 0.6% | Dow Corning |
| Dehyquart A- | Cetrimonium chlonde | ~25% | Cognis |
| Dehyton AB 30 | Coco betaine | ~30% | Cognis |
| Eumulgin HRE 40 | PEG-40 hydrogenated castor oil | 100% | Cognis |
| Euperlan PK 771 | Sodium laureth sulfate + glycol distearate + laureth-10 | 25% + 15% + 5% | Cognis |
| Euperlan PK 900 | PEG-3 distearate + sodium laureth sulfate | 25% + 14% | Cognis |
| Glucamate DOE-120 | PEG-120 methyl glucose dioleate | 100% | Lubrizol |
| Jaguar Excel | Glyceryl glucoside Guar hydroxypropyltrimonium chloride | ~90% | Rhodia |
| Lanette-O | Cetylstearyl alcohol | 100% | Cognis |
| Merquat 550 | Polyquaternium-7 | ~8% | Nalco |
| Opulyn 301 | Styrene/acrylate copolymer | ~40% | Rohm & Haas |
| Polyox WSR-301 | PEG-90M | ~95% | Dow Chemical |
| Rewoderm LI 520-70 | PEG-200 hydrogenated glyceryl palmate | ~70% | Evonik Goldschmidt |
| Rewopol SB CS 50 | Disodium PEG-5 lauryl citrate sulfosuccinate | ~30% | Evonik Goldschmidt |
| Tego Amid S 18 | Stearamidopropyl dimethylamine | 100% | Evonik Goldschmidt |
| Tego Betain F 50 | Cocamidopropyl betaine + glycerol | ~36% + ~3% | Evonik Goldschmidt |
| Texapon N 70 | Sodium laureth sulfate | ~70% | Cognis |
| Ucare Polymer JR 400 | Polyquaternium-10 | ~90% | Dow Chemical |
| Uvinul MS-40 | Benzophenone-4 | 100% | BASF |

Comparative Experiment Shower Gel

The following products were prepared and compared with one another in a subject test:

All Concentration Data in % by Weight

| Phase | INCI | Product A (inventive) | Product B (comparator product) |
|---|---|---|---|
| A | Water, demin. | to 100 | to 100 |
| A | Texapon N70 | 9.00 | 9.00 |
| A | Sodium benzoate | 0.45 | 0.45 |
| A | Sodium salicylate | 0.40 | 0.40 |
| A | Citric acid* | 0.35 | 0.35 |
| A | Rewodern LI 520-70** | 0.10 | 0.10 |
| A | Glycerol | — | 3.50 |
| A | Glycerol glucoside | 7.00 | — |
| B | Eumulgin HRE 40 | 0.50 | 0.50 |
| B | Almond oil | 0.01 | 0.01 |
| B | Cetiol HE | 1.75 | 1.75 |
| B | Perfume | 1.00 | 1.00 |
| $C_1$ | Merquat 550 | 5.00 | 5.00 |
| $C_2$ | Tego Betain F 50 | 16.00 | 16.00 |
| $C_3$ | Opulyn 301 | 1.00 | 1.00 |

*amount variable to establish a pH of 4.8 to 5.3
**amount variable to establish a viscosity in the range of 3000-5000 mPas (measured using HAAKE viscotester VT02 with rotor 1)

Preparation

The ingredients of phase A are mixed until a homogeneous phase is formed.

Eumulgin HRE 40 is melted at a temperature of ca. 40° C. The other raw materials of phase B are added to the Eumulgin HRE 40. The phase is mixed homogeneously and added to phase A.

The addition of the ingredients of phase C is carried out with stirring, in the order stated.

Results

| Criterion | Product A better | No difference | Product B better |
|---|---|---|---|
| Scent impression | 2 | 7 | 0 |
| Consistency | 4 | 5 | 0 |
| Amount of lather | 5 | 4 | 0 |
| Quality of lather | 6 | 3 | 0 |
| Skin feel during washing | 8 | 1 | 0 |
| Ability to be rinsed off | 2 | 7 | 0 |
| Skin feel after use | 3 | 6 | 0 |

7 of 9 subjects assessed the organoleptic properties of inventive product A to be better overall than the organoleptic properties of comparator product B. The other subjects were unable to establish any difference.

5 of 9 subjects perceived the skin feel of inventive product A to be less greasy-slippery than the skin feel of the comparator product B. The other subjects were unable to establish any difference.

It is clear to see that the inventive product A is distinctly superior to the comparator product in respect of all the features.

Comparative Experiment Shampoo

The following products were prepared and compared with one another in a subject test:

All Concentration Data in % by Weight

| Phase | INCI | Product A (inventive) | Product B (comparator product) |
|---|---|---|---|
| A | Water, demin. | to 100 | to 100 |
| A | Texapon N 70 | 12.00 | 12.00 |
| A | Tego Betain F 50 | 9.00 | 9.00 |
| A | Rewopol SB CS 50 | 7.50 | 7.50 |
| A | Sodium benzoate | 0.40 | 0.40 |
| A | Sodium salicylate | 0.40 | 0.40 |
| A | Glycerol | — | 3.50 |
| A | Glyceryl glucoside | 7.00 | — |
| B | Eumulgin HRE 40 | 0.40 | 0.40 |
| B | Perfume | 0.70 | 0.70 |
| $C_1$ | Euperlan PK 900 | 6.00 | 6.00 |
| $C_2$ | Sodium chloride* | 1.00 | 1.00 |
| $C_3$ | Citric acid** | 0.05 | 0.05 |

*amount variable to establish a viscosity in the range of 3000-4500 mPas (measured using a HAAKE viscotester VT02 with rotor 1)
**amount variable to establish a pH of 4.8 to 5.8

Preparation

The ingredients of phase A are mixed with one another until a homogeneous phase is formed.

Eumulgin HRE 40 is melted at a temperature of ca. 40° C. The perfume is added to the Eumulgin HRE 40. The phase is mixed homogeneously and added to phase A.

The addition of the ingredients of phase C is carried out in the order stated. The mixture is stirred until a homogeneous shampoo is formed.

Results

| Criterion | Product A better | No difference | Product B better |
|---|---|---|---|
| Scent impression | 1 | 8 | 0 |
| Consistency | 4 | 5 | 0 |
| Amount of lather | 6 | 3 | 0 |
| Quality of lather | 6 | 3 | 0 |
| Ability to be rinsed off | 4 | 5 | 0 |
| Care performance | 6 | 2 | 0 |
| Combability | 5 | 4 | 0 |

5 of 9 subjects perceived the organoleptic properties of inventive product A to be better overall than the organoleptic properties of comparator product B. The other subjects were unable to establish any difference.

4 of 9 subjects perceived the skin feel of the inventive product A to be less greasy-slippery than the skin feel of the comparator product B. One subject perceived the skin feel of the comparator product B to be less greasy-slippery than the skin feel of the inventive product A. The other subjects were unable to establish any difference.

It is clear to see that the inventive product A is distinctly superior to the comparator product in respect of all the features.

Stability

The viscosities of the inventive product A and of the comparator product B were measured at room temperature (25° C.) and compared with the viscosity following 1 day's and 7 days' storage of the samples at a temperature of −20° C. (in each case measured using a HAAKE viscotester VT02 with rotor 1). Before measuring the samples stored at −20° C., these were stored for one day at 25° C. and measured at this temperature.

|  | Product A (inventive) | Product B (comparator product) |
|---|---|---|
| Viscosity at 25° C. | 3500 mPas | 3200 mPas |
| Viscosity after 1 day's storage at −20° C. | 3300 mPas | 2200 mPas |
| Viscosity after 7 days' storage at −20° C. | 3350 mPas | 2350 mPas |

It is clearly shown that the viscosity of the inventive product A remains almost constant independent of the storage at −20° C., while the viscosity of the comparator product B declines by ca. 30% on storage at −20° C. The use of glyceryl glucoside leads to an increased stability of the products.

Example Formulations
Shampoo Preparations
All Concentration Data in % by Weight

| Phase | INCI | 1.1 | 1.2 | 1.3 | 1.4 |
|---|---|---|---|---|---|
| A | Water, demin | to 100 | to 100 | to 100 | to 100 |
| A | Texapon N 70 | 10.50 | 12.00 | 6.50 | 13.00 |
| A | Rewopol SB CS 50 | — | 7.25 | — | — |
| A | Tego Betain F 50 | 11.50 | 9.50 | 13.00 | 10.00 |
| A | Merquat 550 | 2.50 | — | 2.50 | 2.50 |
| A | Panthenol | — | 0.50 | 1.00 | 0.10 |
| A | Sodium benzoate | 0.50 | 0.30 | 0.40 | 0.40 |
| A | Sodium salicylate | 0.10 | 0.20 | 0.20 | 0.20 |
| A | Glyceryl glucoside | 0.05 | 0.50 | 1.00 | 5.00 |
| B | Ucare Polymer JR 400 | 0.10 | 0.30 | 0.10 | — |
| B | Water, demin. | 15.00 | 15.00 | 15.00 | — |
| C | Water, demin. | — | 10.00 | 10.00 | — |
| C | Sodium hydroxide soln. 45% | — | 0.01 | 0.01 | — |
| C | Jaguar Excel | — | 0.10 | 0.12 | — |
| C | Citric acid | — | 0.03 | 0.03 | — |
| D | Eumulgin HRE 40 | 0.30 | 0.40 | 0.30 | 0.40 |
| D | Jojoba oil | 0.01 | 0.01 | 0.01 | 0.01 |
| D | Perfume | 0.60 | 0.80 | 0.90 | 0.70 |
| $E_1$ | Euperlan PK 900 | 4.00 | 6.00 | — | — |
| $E_2$ | Sodium chloride* | 2.20 | 1.80 | 1.80 | 1.30 |
| $E_3$ | Citric acid** | 0.15 | 0.10 | 0.40 | 0.22 |

*amount variable to establish a viscosity in the range of 3000-4500 mPas (measured using a HAAKE viscotester VT02 with rotor 1)
**amount variable to establish a pH of 4.8 to 5.8

The ingredients of phase A are mixed with one another until a homogeneous phase is formed.

Ucare Polymer JR 400 is dispersed in the water of phase B. Phase B is heated to ca. 70° C. with stirring until a clear solution is formed. Phase B is cooled and added to phase A.

The water of phase C is mixed with the sodium hydroxide solution. Jaguar Excel is slowly interspersed with stirring. The mixture is then heated to 70° C. and stirred until a homogeneous phase has been formed. The citric acid is added with stirring. Phase C is cooled and added to phase A.

Eumulgin HRE 40 is melted at a temperature of ca. 40° C. The other raw materials of phase D are added to the Eumulgin HRE 40. The phase is homogeneously mixed and added to phase A.

The addition of the ingredients of phase E is carried out in the order stated. The mixture is stirred until a homogeneous shampoo is formed.

Shower Gel Preparations
All Concentration Data in % by Weight

| Phase | INCI | 2.1 | 2.2 | 2.3 | 2.4 | 2.5 |
|---|---|---|---|---|---|---|
| A | Water, demin. | to 100 | to 100 | to 100 | to 100 | to 100 |
| A | Texapon N70 | 9.00 | 11.00 | 7.00 | 4.00 | 6.50 |
| A | Sodium benzoate | 0.45 | 0.45 | 0.45 | 0.45 | 0.45 |
| A | Sodium salicylate | 0.40 | 0.40 | 0.40 | — | 0.40 |
| A | Citric acid* | 0.35 | 0.35 | 0.35 | 0.35 | 0.50 |
| A | Rewoderm LI 520-70** | 0.10 | 0.10 | 0.10 | 0.10 | — |
| A | Glucamate DOE-120 | — | — | — | — | 0.03 |
| A | Glycerol | — | — | 1.00 | — | 1.00 |
| A | Uvinul MS-40 | — | — | — | 0.50 | — |
| A | Glyceryl glucoside | 0.01 | 0.10 | 3.00 | 1.00 | 1.00 |
| B | Eumulgin HRE 40 | 0.50 | 0.50 | 0.50 | 0.50 | 0.25 |
| B | Almond oil | 0.01 | 0.01 | — | — | 0.20 |
| B | Sunflower oil | — | — | 0.01 | 0.04 | — |
| B | Avocado oil | — | — | — | 0.02 | — |
| B | Cetiol HE | 1.75 | 2.00 | 2.50 | 2.00 | 1.00 |
| B | Polyox WSR-301 | — | — | — | 0.10 | — |
| B | Perfume | 1.00 | 1.00 | 1.00 | 1.00 | 0.20 |
| $C_1$ | Merquat 550 | 3.00 | 6.00 | 4.00 | 5.00 | — |
| $C_2$ | Tego Betain F 50 | 15.00 | 20.00 | 12.00 | 25.00 | 15.00 |
| $C_3$ | Opulyn 301 | 1.00 | 1.00 | 1.00 | — | — |
| $C_4$ | Euperlan PK 900 | — | — | — | 4.00 | — |
| $C_5$ | Euperlan PK 771 | — | — | — | — | 4.00 |

*amount variable to establish a pH of 4.8 to 5.3
**amount variable to establish a viscosity in the range of 3000-5000 mPas (measured using a HAAKE viscotester VT02 with rotor 1)
The ingredients of phase A are mixed until a homogeneous mixture is formed.

The ingredients of phase A are mixed until a homogeneous mixture is formed.

Eumulgin HRE 40 is melted at a temperature of ca. 40° C. The other raw materials of phase B are added to the Eumulgin HRE 40. The phase is homogeneously mixed and added to phase A.

The addition of the ingredients of phase C is carried out in the order stated, with stirring.

Rinse-Off Conditioner
All Concentration Data in % by Weight

| Phase | INCI | 3.1 | 3.2 |
|---|---|---|---|
| A | Water, demin. | to 100 | to 100 |
| A | Dehyton AB 30 | 1.00 | 1.00 |
| A | Sodium benzoate | 0.30 | 0.30 |
| A | Lactic acid* | 0.60 | 0.40 |
| A | Dehyquart A-CA | 4.00 | 2.00 |
| A | Sodium chloride | 0.07 | 0.07 |
| A | Glyceryl glucoside | 0.10 | 1.00 |
| B | Water, demin. | 10.00 | 10.00 |
| B | Sodium hydroxide soln. 45% | 0.02 | 0.02 |
| B | Jaguar Excel | 0.10 | 0.10 |
| B | Citric acid | 0.04 | 0.04 |
| C | Lanette O | 5.00 | 5.20 |
| C | Tego Amid S 18 | 1.50 | 1.00 |
| D | DC 5-7139 | 4.60 | 1.50 |
| E | Perfume | 0.80 | 0.70 |

*amount variable to establish a pH of the water phase of 3.8 to 4.8

The raw materials of phase A are mixed with one another and heated to 80° C. The water of phase B is mixed with the sodium hydroxide solution. Jaguar Excel is slowly interspersed with stirring. The mixture is then heated to 70° C. and stirred until a homogeneous phase has been formed. The citric acid is added with stirring. Phase B is added to phase A.

The raw materials of phase C are heated to 80° C. in a kitchen aid and homogeneously mixed with stirring. Phase A is added to phase C.

Phase A and phase C are mixed with one another in a kitchen aid and cooled. Phase C is added at 40° C. and phase D at 30° C. The mixture is stirred until a homogeneous conditioner is formed.

The viscosity of the conditioner is 3000-4000 mPas (measured using a HAAKE viscotester VT02 with rotor 1).

What is claimed is:

1. An active ingredient combination, wherein the combination comprises
   (i) one or more acidic preservatives selected from salicylic acid, benzoic acid, propionic acid, dehydroacetic acid, sorbic acid, and physiologically compatible water-soluble metal salts thereof,
   and
   (ii) one or more glucosyl glycerides,
a molar ratio (i):(ii) being from 100:1 to 1:100.

2. The combination of claim 1, wherein the molar ratio (i):(ii) is from 50:1 to 1:50.

3. The combination of claim 1, wherein the molar ratio (i):(ii) is from 20:1 to 1:20.

4. The combination of claim 1, wherein (i) comprises one or more preservatives selected from salicylic acid, benzoic acid, dehydroacetic acid, and physiologically compatible water-soluble metal salts thereof.

5. A cosmetic preparation, wherein the preparation comprises the active ingredient combination of claim 1.

6. The preparation of claim 5, wherein the preparation comprises from 0.005% to 15.00% by weight of the one or more glucosyl glycerides (ii), based on a total weight of the preparation.

7. The preparation of claim 5, wherein the preparation comprises from 0.01% to 12.00% by weight of the one or more glucosyl glycerides (ii), based on a total weight of the preparation.

8. The preparation of claim 6, wherein the preparation comprises from 0.005% to 5% by weight of the one or more acidic preservatives (i), based on a total weight of the preparation.

9. The preparation of claim 7, wherein the preparation comprises from 0.01% to 3% by weight of the one or more acidic preservatives (i), based on a total weight of the preparation.

10. The preparation of claim 5, wherein the preparation further comprises one or more surfactants.

11. The preparation of claim 10, wherein the preparation comprises from 1% to 20% by weight of one or more anionic surfactants, based on a total weight of the preparation.

12. The preparation of claim 10, wherein the preparation comprises from 5% to 12% by weight of one or more anionic surfactants, based on a total weight of the preparation.

13. The preparation of claim 11, wherein the one or more anionic surfactants comprise sodium lauryl ether sulfate.

14. The preparation of claim 12, wherein the one or more anionic surfactants comprise sodium lauryl ether sulfate.

15. The preparation of claim 5, wherein the preparation further comprises from 1% to 20% by weight of one or more amphoteric surfactants, based on a total weight of the preparation.

16. The preparation of claim 15, wherein the one or more amphoteric surfactants comprise cocamidopropyl betaine.

17. The preparation of claim 11, wherein the preparation further comprises from 1% to 20% by weight of one or more amphoteric surfactants, based on a total weight of the preparation.

18. The preparation of claim 5, wherein the preparation further comprises one or more non-ionic surfactants.

19. The preparation of claim 5, wherein the preparation is a shower gel.

20. The preparation of claim 5, wherein the preparation is a shampoo.

* * * * *